(12) United States Patent
Loverich et al.

(10) Patent No.: US 8,349,611 B2
(45) Date of Patent: Jan. 8, 2013

(54) RESONANT SENSORS AND METHODS OF USE THEREOF FOR THE DETERMINATION OF ANALYTES

(75) Inventors: Jacob J. Loverich, State College, PA (US); Jeremy E. Frank, Pine Grove Mills, PA (US); Peter A. Nagy, Newtown Square, PA (US)

(73) Assignee: Leversense LLC, Newtown Square, PA (US)

( * ) Notice: Subject to any disclaimer, the term of this patent is extended or adjusted under 35 U.S.C. 154(b) by 0 days.

(21) Appl. No.: 12/707,254

(22) Filed: Feb. 17, 2010

(65) Prior Publication Data
US 2010/0207602 A1 Aug. 19, 2010

Related U.S. Application Data

(60) Provisional application No. 61/153,119, filed on Feb. 17, 2009.

(51) Int. Cl.
*G01N 33/551* (2006.01)
(52) U.S. Cl. .......... 436/86; 73/24.01; 73/24.06; 73/579; 422/82.01; 436/94; 436/178; 436/512; 436/524; 436/527
(58) Field of Classification Search .......... 73/24.01, 73/24.06, 579; 422/82.01; 436/86, 94, 178, 436/512, 524, 527
See application file for complete search history.

(56) References Cited

U.S. PATENT DOCUMENTS

| | | | | |
|---|---|---|---|---|
| 2,224,891 A | * | 12/1940 | Wright | 310/348 |
| 3,678,309 A | * | 7/1972 | Choffat | 310/353 |
| 4,104,553 A | * | 8/1978 | Engdahl et al. | 310/352 |
| 4,137,511 A | * | 1/1979 | Jones | 333/186 |
| 4,242,096 A | * | 12/1980 | Oliveira et al. | 436/500 |
| 4,350,918 A | * | 9/1982 | Sato | 310/367 |
| 4,357,554 A | * | 11/1982 | Peters | 310/367 |
| 4,445,065 A | * | 4/1984 | Albert | 310/321 |
| 4,447,753 A | * | 5/1984 | Ochiai | 310/312 |
| 4,494,033 A | * | 1/1985 | Morse et al. | 310/352 |
| 4,564,744 A | * | 1/1986 | Valentin | 219/210 |
| 4,609,844 A | * | 9/1986 | Nakamura et al. | 310/321 |
| 4,631,437 A | * | 12/1986 | Ballato | 310/369 |
| 4,741,200 A | * | 5/1988 | Hammerle | 73/54.25 |
| 4,870,313 A | * | 9/1989 | Hirama et al. | 310/320 |
| 4,951,510 A | * | 8/1990 | Holm-Kennedy et al. | 73/862.041 |
| 4,999,284 A | * | 3/1991 | Ward et al. | 435/4 |
| 5,056,366 A | * | 10/1991 | Fersht et al. | 73/504.15 |
| 5,179,499 A | * | 1/1993 | MacDonald et al. | 361/313 |
| 5,218,260 A | * | 6/1993 | Kawashima | 310/361 |

(Continued)

FOREIGN PATENT DOCUMENTS
WO 9428452 12/1994
(Continued)

OTHER PUBLICATIONS

Wan, J. et al, Sensors and Actuators B 2007, 127, 559-566.*

(Continued)

*Primary Examiner* — Arlen Soderquist
(74) *Attorney, Agent, or Firm* — Patrick J. Hagan; Dann, Dorfman, Herrell and Skillman, PC

(57) ABSTRACT

Resonant sensors, preferably having floating bilayer symmetry, and their methods of use is determining the presence, amount or binding kinetics of an analyte of interest in a test sample are disclosed. The test sample may be a liquid or gas.

41 Claims, 9 Drawing Sheets

U.S. PATENT DOCUMENTS

| | | | | |
|---|---|---|---|---|
| 5,343,748 A * | 9/1994 | Mozgowiec et al. | | 73/497 |
| 5,501,986 A * | 3/1996 | Ward et al. | | 436/525 |
| 5,658,732 A * | 8/1997 | Ebersole et al. | | 435/6 |
| 5,705,399 A * | 1/1998 | Larue | | 436/501 |
| 5,719,324 A * | 2/1998 | Thundat et al. | | 73/24.01 |
| 5,780,727 A * | 7/1998 | Gimzewski et al. | | 73/105 |
| 5,789,845 A * | 8/1998 | Wadaka et al. | | 310/334 |
| 5,852,229 A * | 12/1998 | Josse et al. | | 73/24.06 |
| 5,912,608 A * | 6/1999 | Asada | | 335/222 |
| 6,033,852 A * | 3/2000 | Andle et al. | | 435/6 |
| 6,388,789 B1 * | 5/2002 | Bernstein | | 359/198.1 |
| 6,632,698 B2 * | 10/2003 | Ives | | 438/52 |
| 6,717,336 B2 * | 4/2004 | Kawashima | | 310/367 |
| 6,866,819 B1 * | 3/2005 | Chandra et al. | | 422/50 |
| 6,914,279 B2 * | 7/2005 | Lu et al. | | 506/39 |
| 7,148,017 B1 * | 12/2006 | Craighead et al. | | 435/7.1 |
| 7,181,977 B2 * | 2/2007 | Thompson et al. | | 73/777 |
| 7,210,332 B2 * | 5/2007 | Kolosov et al. | | 73/24.06 |
| 7,232,545 B2 * | 6/2007 | Centanni et al. | | 422/3 |
| 7,233,218 B2 * | 6/2007 | Park et al. | | 333/133 |
| 7,312,674 B2 * | 12/2007 | Duwel et al. | | 333/186 |
| 7,329,536 B2 * | 2/2008 | Zeng et al. | | 435/287.2 |
| 7,350,367 B2 * | 4/2008 | Matsiev et al. | | 62/129 |
| 7,458,265 B2 | 12/2008 | Shih et al. | | |
| 7,468,608 B2 * | 12/2008 | Feucht et al. | | 324/633 |
| 7,492,241 B2 * | 2/2009 | Piazza et al. | | 333/189 |
| 7,586,239 B1 * | 9/2009 | Li et al. | | 310/323.02 |
| 7,639,105 B2 * | 12/2009 | Ayazi et al. | | 333/186 |
| 7,667,369 B2 * | 2/2010 | Haskell et al. | | 310/313 R |
| 7,691,583 B2 * | 4/2010 | Craighead et al. | | 435/7.1 |
| 7,779,707 B2 * | 8/2010 | Shih et al. | | 73/862.639 |
| 7,791,432 B2 * | 9/2010 | Piazza et al. | | 333/186 |
| 7,888,843 B2 * | 2/2011 | Ayazi et al. | | 310/324 |
| 7,898,158 B1 * | 3/2011 | Li et al. | | 310/351 |
| 7,915,974 B2 * | 3/2011 | Piazza et al. | | 333/186 |
| 8,035,280 B2 * | 10/2011 | Li et al. | | 310/351 |
| 2002/0028440 A1 * | 3/2002 | Willner et al. | | 435/6 |
| 2002/0081587 A1 * | 6/2002 | Hwang et al. | | 435/6 |
| 2003/0006853 A1 * | 1/2003 | Yamanaka et al. | | 331/158 |
| 2004/0187580 A1 * | 9/2004 | Nozaki | | 73/580 |
| 2005/0001514 A1 * | 1/2005 | Takeuchi et al. | | 310/328 |
| 2005/0003560 A1 * | 1/2005 | Zeng et al. | | 436/527 |
| 2005/0016276 A1 * | 1/2005 | Guan et al. | | 73/579 |
| 2005/0140467 A1 * | 6/2005 | Duwel et al. | | 333/189 |
| 2005/0148065 A1 * | 7/2005 | Zhang et al. | | 435/287.2 |
| 2006/0014270 A1 * | 1/2006 | Mansson et al. | | 435/287.2 |
| 2006/0073077 A1 * | 4/2006 | Centanni | | 422/82.01 |
| 2006/0196253 A1 * | 9/2006 | Crawley et al. | | 73/53.01 |
| 2006/0223171 A1 * | 10/2006 | Craighead et al. | | 435/287.2 |
| 2006/0257286 A1 * | 11/2006 | Adams | | 422/82.01 |
| 2006/0273867 A1 * | 12/2006 | Piazza et al. | | 333/189 |
| 2006/0290449 A1 * | 12/2006 | Piazza et al. | | 333/187 |
| 2007/0089515 A1 | 4/2007 | Shih et al. | | |
| 2007/0169553 A1 | 7/2007 | Mutharasan et al. | | |
| 2008/0034840 A1 | 2/2008 | Mutharasan et al. | | |
| 2008/0035180 A1 | 2/2008 | Mutharasan et al. | | |
| 2008/0100176 A1 * | 5/2008 | Haskell et al. | | 310/313 R |
| 2009/0072663 A1 * | 3/2009 | Ayazi et al. | | 310/320 |
| 2009/0108959 A1 * | 4/2009 | Piazza et al. | | 333/189 |
| 2009/0134319 A1 * | 5/2009 | Sprague et al. | | 250/234 |
| 2009/0144963 A1 * | 6/2009 | Piazza et al. | | 29/594 |
| 2009/0203000 A1 * | 8/2009 | Mutharasan et al. | | 435/6 |
| 2009/0307884 A1 * | 12/2009 | Duwel et al. | | 29/25.35 |
| 2010/0060111 A1 * | 3/2010 | Ayazi et al. | | 310/367 |
| 2010/0116161 A1 * | 5/2010 | Shilpiekandula et al. | | 101/407.1 |
| 2011/0133848 A1 * | 6/2011 | Ayazi et al. | | 331/158 |
| 2011/0133856 A1 * | 6/2011 | Piazza et al. | | 333/189 |
| 2011/0148252 A1 * | 6/2011 | Li et al. | | 310/321 |

FOREIGN PATENT DOCUMENTS

| | | | |
|---|---|---|---|
| WO | 0225630 A3 | 3/2002 | |
| WO | 2007123967 A2 | 11/2007 | |

OTHER PUBLICATIONS

G. Campbell et al., "Detection of pathogen *Escherichia coli* O157:H7 using self-excited PZT-glass microcantilevers", Biosensors and Bioelectronics, 21: 462-473 (2005).

G. Campbell et al., "Detection and quantification of proteins using self-excited PZT-glass millimeter-sized cantilever", Biosensors and Bioelectronics, 21: 597-607 (2005).

G. Campbell et al., "Method of Measuring *Bacillus anthracis* Spores in the Prese4nce of Copious Amounts of *Bacillus thuringiensis* and *Bacillus cereus*", Anal. Chem., 79: 1145-1152 (2007).

K. Rijal et al., "PEMC-based Method of Measuring DNA Hybridization at Femtomolar Concentration Directly in Human Serum and in the Presence of Copious Noncomplementary Strands", Anal. Chem., 79: 7392-7400 (2007).

D. Maraldo et al., "Method for Label-Free Detection of Femtogram Quantities of Biologics in Flowing Liquid Samples", Anal. Chem., 79: 2762-2770 (2007).

D. Maraldo et al., "Method for Quantification of a Prostate Cancer Biomarker in Urine without Sample Preparation", Anal., 79: 7683-7690 (2007).

G. Campbell et al., "Near real-time detection of Cryptosporidium parvum oocyst by IgM-functionalized piezoelectric-excited millimeter-sized cantilever biosensor", Biosensors and Bioelectronics, 23: 1039-1045 (2008).

\* cited by examiner

US 8,349,611 B2

RESONANT SENSORS AND METHODS OF USE THEREOF FOR THE DETERMINATION OF ANALYTES

CROSS-REFERENCE TO RELATED APPLICATIONS

The present application claims the benefit of U.S. Provisional Patent Application No. 61/153,119, filed Feb. 17, 2009, the entire disclosure of which is incorporated by reference herein.

BACKGROUND OF THE INVENTION

The present invention relates to resonant sensors and in particular to biosensors useful for the qualitative and quantitative determination of one or more analytes, e.g., a specific protein, carbohydrate, glycoprotein, protein complex, nucleic acid molecules, (DNA and RNA) mycoplasma, virus, bacterium, yeast, mammalian cell, parasites, cysts, prions, or phospholipid, in a test sample suspected of containing such analyte(s).

A host of analytical techniques have been developed for the detection of biomolecules, pathogens and the like. Such techniques include surface plasmon resonance (SPR), polymerase chain reaction (PCR), enzyme-linked immunoassay (ELISA), and immuno-magnetic beads, to name a few. Although widely used, these techniques are not very sensitive and require extensive sample preparation, especially with complex or unpurified biological samples. Moreover, most biosensing platforms now in commercial use are not capable of making analyte determinations by measuring changes in mass on a sensor surface.

Considerable research has been devoted to the advancement of microscale biosensor technology, with a view toward achieving analyte detection with high specificity, sensitivity and reproducibility, but at a reduced cost compared to SPR, PCR, ELISA and the like.

A biosensor is a device in which a biological component, such as a nucleic acid probe, an antibody or other member of a specific binding pair, and a transducer or detector (i.e. optical, piezoelectric, electrochemical, etc.) component are integrated to generate a measurable signal. Biosensing devices have been proposed for use in a wide variety of applications, including medical diagnostics (determination/ quantification of biomarkers present in bodily fluid), environmental testing (pathogens in drinking water), assessing food safety (*Listeria, Cyrptosporidum, Giardia* and *E. coli* contamination) and in biodefense (monitoring bioterrorism agents). One such device is a piezoelectric-excited millimeter-sized cantilever (PEMC) sensor that measures a change in mass based on a resonance frequency shift, as described in detail in U.S. Patent Application Publication No. 2007/ 0169553 of Mutharasan et al. Briefly, the sensor consists of a piezoelectric (P) or active layer, e.g., lead zirconate titanate (PZT), adhesively bonded to a non-piezoelectric (NP) or passive layer of a few millimeters in length and 1 mm in width. The active layer is mounted in or on a suitable support by means of a mounting material, such as non-conducting epoxy. The active layer and the passive layer overlay, in shingle fashion, so that the respective layers are not coextensive. The PZT layer of the cantilever serves both as an actuating and as a sensing element. When an electric field is applied across the thickness of the PZT layer, it undergoes three dimensional deformation. Deformation occurs primarily along the planar dimensions of the PZT layer, because of geometrical and associated constraints, causing the base non-piezoelectric layer to flex. If the field alternates, the sensor experiences flexural oscillations. The sensor resonates when the excitation frequency coincides with the natural frequency (mechanical) of the cantilever beam. At resonance, the cantilever undergoes higher than normal bending stresses and the PZT layer, being electro-mechanically active, exhibits a sharp change in electrical impedance. The phase angle between the excitation voltage and the resulting current changes significantly, and is conveniently measured using an impedance analyzer. The sensing response is recorded by measuring changes in resonance frequency of the vibrating sensor.

PEMC sensors have been shown to be useful for detection of water-borne pathogens, such as *E. coli*, and for detection and direct quantification of protein-protein binding interactions. Campbell & Mutharasan, Biosensors and Bioelectronics, 21; 462-473 and 597-607 (2005). See also Campbell and Mutharasan, Anal. Chem., 79: 1145-52 (2007), which reports the measurement of *B. anthracis* in the presence of substantial concentrations of *B. thuringiensis* and *B. cereus*.

PEMC sensors have a practical advantage over sensor platforms based on quartz crystal microbalance (QCM), involving a disk device that uses thickness-mode resonance for sensing. Although quartz is a weak piezoelectric material, it is widely used as a layer thickness monitor due in part to the availability of large quartz single crystals from which the membranes are made. The typical mass detection sensitivity of a 5 MHz QCM device having a minimum detectable mass density (DMD) of $10^{-9}$ g/cm$_2$ is about $10^{-8}$ g/Hz, which is about four orders of magnitude less sensitive than PEMC devices. Thus, QCM analysis is of limited value when the analyte is present at low concentration together with a high level of contaminants.

It is also quite common to fabricate cantilever sensors, especially micro- and nano-scale cantilever sensors, using microelectromechanical systems (MEMS) or other wafer level etching techniques, whereby the cantilever "finger" is integral with, and of the same material as the base or anchor. Consequently, the stiffness of the "finger" and base will be identical so that resonant frequency modes, observed by changes in the "finger" impedance will be highly complicated and minimally useable. The effective mass of the sensor will also be relatively high, which will make the sensitivity comparatively low and any resonant frequencies will also be comparatively lower than sensors which are not integrally fabricated in this way.

Another piezoelectric cantilever-type sensor is described in U.S. Patent Application Publication No. 2007/0089515 of Shih et al. In an embodiment of that sensor intended for bio-detection, antibodies or other specific receptors of target antigens may be immobilized on the cantilever surface, preferably on the non-pizeoelectric tip. Binding of the target antigens to the cantilever surface increases the cantilever mass. Detection of target antigens is achieved by monitoring the cantilever's resonance frequency and determining the resonance frequency shift that is due to the mass of the adsorbed target antigens on the cantilever surface. The asymmetrical cantilever design, incorporating an overlapping non-peizoelectric tip, is described as enhancing the sensitivity of the sensor.

Although the piezoelectric cantilever sensors of the prior art are satisfactory in many respects, the excess length resulting from the overlap between the piezoelectric layer and non-piezoelectric layer adds parasitic geometry to the sensor which degrades key aspects of the sensor performance. The overlap portion in certain embodiments (P>NP), together with the mounting material and electrode attachment, increases the effective mass of the sensor, thus causing a corresponding reduction in sensitivity. Furthermore, the mounting material in the piezoelectric cantilever sensors of the prior art produces a damping effect, which decreases the quality (Q) factor of the signal produced, i.e. the ratio of resonance peak frequency to the resonance peak width at half peak height. The prior art sensors also vary in sensitivity along their length, which adds uncertainty to the measurement fidelity. The asymmetry of the prior art sensors also tends to introduce unwanted or degenerate modes into the detection signal. Damping is added to the prior art sensors, to convolute the degenerate modes. This can lead to variations in sensitivity, depending on the original separation of the modes and the location of the analyte receptors. Such variations can completely obscure the sensing signal or at least diminish the signal-to-noise ratio. Finally, the prior art sensors do not suggest where the vibrational nodes, present in all vibrating structures, are to be found. These nodes will be sites where the attachment of a target analyte will not register a sensor response. Hence, if these vibrational node sites are unknown, or are not excluded as a sensing region, the sensor will be less accurate and have greater variability, as compared with a sensor in which the node sites are identified and excluded from the sensing region.

Thus, a need exists for improved resonant sensor designs which provide sensitivity at least comparable to the biosensors of the prior art, with increased Q factor, and which can be fabricated with high reproducibility and at relatively low cost.

SUMMARY OF THE INVENTION

In accordance with one aspect of the present invention, there is provided a resonant sensor for determining the presence, amount or binding kinetics of an analyte in a test medium. The sensor is operable under the influence of an activating force field and comprises an active, deformable planar member that serves as a sensing element, having a resonant mode for analyte determination and one or more axis of symmetry. The sensor also comprises a capture agent for the analyte of interest associated with at least one exterior surface of the sensing element. The influence of the activating force field on the resonant sensor is such as to cause the sensing element, with its associated capture agent, to vibrate at a determinable resonance frequency, and to induce in the sensing element a uniform bending or in-plane stretching parallel or perpendicular to the one or more axis of symmetry.

In a preferred embodiment, a passive, deformable planar member is attached to and coextensive with the active, deformable planar member, and forms therewith a pliable layered sensing element. The in-plane shape of a sensing element formed in this way may be rectangular or circular. The activating force operating on the active member will thereby induce a uniform bending moment along an axis of symmetry.

The active planar member may comprise a piezoelectric material or an electrostrictive material, and in each case the activating force field is an electric field. The active planar member may alternatively comprise a magnetostrictive material, in which case the activating force field is a magnetic field.

In operation, the activating force field activates the active, deformable planar member, thereby causing portions of the sensing element adjacent to nodal points or lines (which are characteristic of the resonant mode of the active planar member) to move relative to the nodes.

In accordance with another aspect of this invention, there is provided a system for determining the presence, or amount or binding kinetics of an analyte in a test medium, which system comprises an assembly of concatenated resonant sensors having the characteristics described herein, and a device operable to determine the resonance frequency of the resonant sensors in the assembly. According to a preferred embodiment, each of the resonant sensors in the assembly is operable under the influence of a common activating force field, and the resonance frequency at which the sensing element of each of the resonant sensors vibrates is determined by a common frequency determining device. In another preferred embodiment, each of the resonant sensors in the assembly has disposed on the surface thereof a capture agent which is different from the capture agent on any other sensing element in the assembly, such that each resonant sensor captures a different analyte. At least one of the sensing elements in the assembly could serve as an environmental reference and would have no capture agents disposed on the sensing surface.

In yet another aspect, the present invention provides a method for determining an analyte in a test medium suspected to contain such analyte, which involves the following steps:
  a. providing at least one resonant sensor having the features described herein, which includes a capture agent comprising a specific binding pair member that binds the analyte of interest;
  b. establishing a reference or baseline resonance frequency for the resonant sensor; and or using a second sensor with no capture agent to provide the baseline resonant frequency;
  c. contacting the sensor with a medium suspected to contain the analyte of interest in a flow cell, microtiter or other sample format, for a time sufficient for the specific binding pair member to bind the analyte of interest present in said medium;
  d. determining a test resonance frequency of the sensor after contact with the test medium which is indicative of the presence or absence of the analyte of interest.

A shift or change in the resonance frequency as a result of analyte binding to the capture agent provides a qualitative indication of target analyte in the test medium, whereas measurement of the difference between the reference and test frequencies gives a quantitative analyte determination. The difference in frequencies is directly proportional to the mass of the attached analyte.

Sensors embodying the present invention, fabricated with dimensional symmetry, provide a number of important cost, performance and utility advantages over prior art sensors, because the sensors fabricated with these features are "floating" and mechanically decoupled from any base or anchor which would tend to dampen the resonant frequency and increase the effective mass of the sensor. Dampening can diminish the sensing signal to the point of being unusable. By minimizing the effective mass, however, the sensor of the present invention has increased sensitivity. The symmetry of the structure is ideal for enabling a clean resonant frequency signal with little to no noise. For the preferred embodiment having a coextensive structure, mechanical robustness will be enhanced since the structure does not rely solely on an unsupported active planar member, the active materials often being brittle, but rather is fully backed by the passive planar member at any point along its length.

The analyte determination method described herein takes advantage of the unique binding affinities of cells and biomolecules for their specific binding partners. When binding occurs between an analyte of interest and its specific binding pair member immobilized on the layered sensing element of the resonant sensor, the change in certain physical parameters, preferably mass, is measured by transducers producing an electrical signal proportional to the binding interaction. If desired, the kinetics of the binding interaction can be determined using this method. Normally binding kinetics can be determined in two ways. The first involves sequentially exposing a sensor with receptors to a solution containing the analyte of interest until binding equilibrium is reached, followed by a solution with no analyte such that dissolution of the bound analyte occurs. Alternatively, a sensor with associated receptors is exposed to a solution containing the analyte of interest until binding equilibrium occurs. Thereafter, the voltage amplitude of the sensor is increased until the binding energy of receptor-analyte pair is exceeded. This dissociation voltage provides a measure of binding energy. Such binding affinity is typically not measured on cells.

BRIEF DESCRIPTION OF THE DRAWINGS

in FIG. 2A both electrodes extend from the active planar member on one side extending to a base or anchor, whereas in FIG. 2B each electrode extends from a different and opposing end of the active planar member to separate and opposite bases or anchors.

in FIG. 5A both electrodes extend from the active planar member on one and the same side extending to a base or anchor, whereas in FIG. 5B each electrode extends from a different and opposing end of the active planar member to separate and opposite bases or anchors.

in FIG. 7A the in-plane shape of the sensing element is circular and resonating in a bending mode, whereas in FIG. 7B the in-plane shape of the sensing element is rectangular and resonating in a bending mode; and in FIG. 7C the sensor in-plane shape of the sensing element is rectangular and resonating in an extension mode.

DETAILED DESCRIPTION OF THE INVENTION

The resonant sensor of this invention is a dynamic system that uses mechanical resonance as the primary means for detection of analytes. Mechanical resonance corresponds to a dynamic condition in which kinetic and potential energy balance and an amplification in both can occur in response to a given periodic force. The kinetic energy in the system is proportional to the effective mass of the system, which in the case of the sensor is defined by the size and density of the region of the sensing element that is moving during resonance. The potential energy is proportional to the stiffness of the sensor. At resonance the amplification is determined by the loss factor which is the ratio of the energy lost per cycle to the total potential energy that is converted to kinetic energy per cycle. For a dynamic system, the loss factor is directly related to the damping and quality factor (Q) which is inversely proportional to the damping ratio. If the damping ratio is sufficiently high, the system will be critically damped and amplification will not occur at resonance.

A given system can have many resonance conditions that correspond to different ways in which the system can deform and the mass and stiffness remain in harmony. In the case of the sensor, it can undergo bending along the length, extension along the length, twisting along the axis of symmetry, and many other forms of deformation. These various forms of deformation correspond to the natural modes of the system. The frequency that each mode corresponds to is, therefore, defined by the mass and stiffness of the system. The effective mass for a given mode is the modal mass.

The sensor is excited in a resonance mode by means of the active material comprising the sensing element, which, upon actuation, can assume an extension or bending mode of operation. The stiffness in the case of a bending mode of operation is often referred to as the bending or flexural stiffness.

When an analyte is attached to the sensor, the effective mass of the sensor increases but the stiffness remains unchanged. For a given mode, the change in mass provides a shift in its resonance frequency. Because resonance frequency can readily be measured with a very high level of precision, very small changes in the sensor effective mass can be detected.

In order for the sensor to work optimally, features such as a flexible coupling that supports the sensing element must be configured such that they do not alter the key sensing modes or add new resonance modes that hamper detection of the critical sensing mode. Minimizing the modal mass and flexural stiffness of the coupling can reduce its influence on the sensing element. Adding damping such that the coupling is critically damped can also benefit the sensor.

Figure 1:
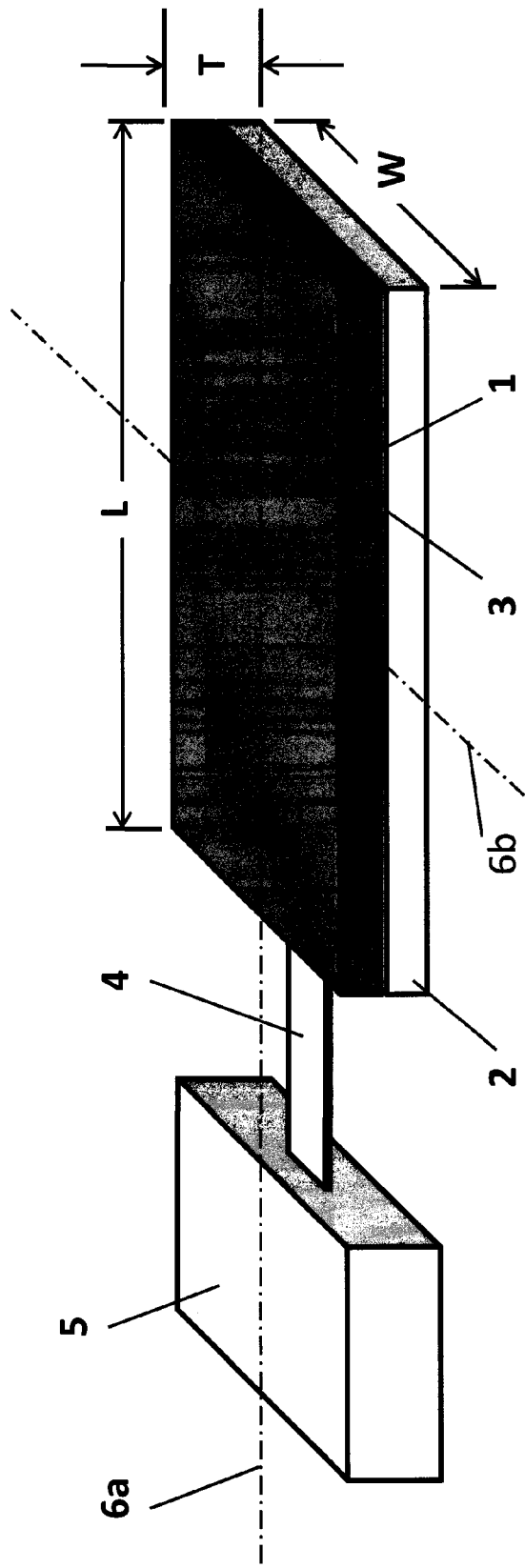
FIG. 1 is a perspective view of a resonant sensor, according to the present invention embodying "floating" bi-layer symmetry, in which the active and passive planar members of the sensing element are coextensive.
Figure 2:
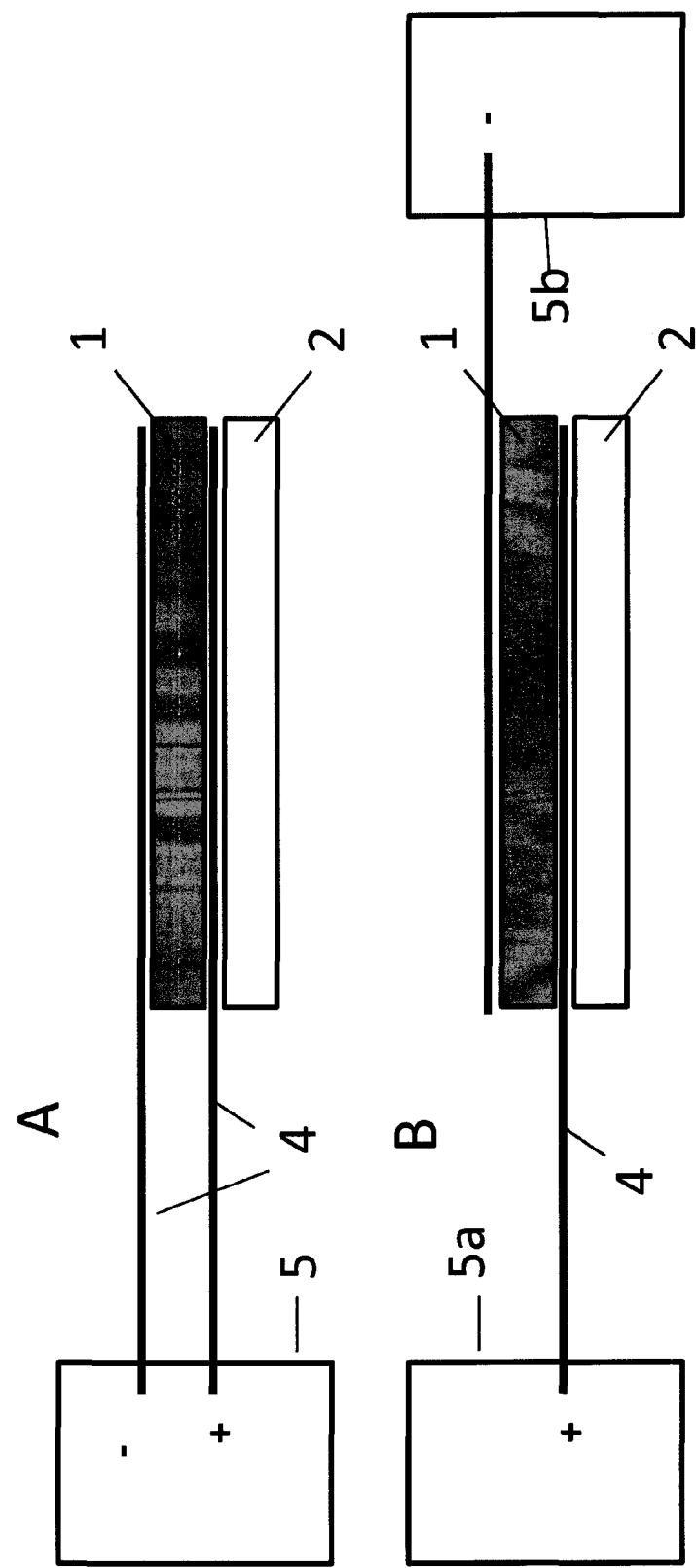
FIG. 2 is a side view of a resonant sensor, according to the present invention embodying "floating" bi-layer symmetry and having alternative electrode configurations with electrodes disposed on opposite faces of the active planar member.

FIGS. 1 and 2 are illustrations of resonant sensors with floating bi-layer symmetry. This floating assembly design is a preferred embodiment in which the active planar member 1 and passive planar member 2, which are joined by a suitable bonding material 3, are coextensive, with both a longitudinal (6a) and a lateral (6b) axis of symmetry. The symmetry of this design will create a very clean spectrum with typically one dominant resonant frequency in the target detection frequency range. Asymmetric structures, by contrast, will show the presence of many resonant frequencies ("noise") within the dynamic frequency range of the resonant sensor, making it difficult or impossible to separate the resonant frequency used for detection from the divergent frequencies. Furthermore, minimizing the mass and stiffness of the flexure 4 or attachment points, in this case the electrodes to the base(s) or substrate(s) 5 has three benefits. First, the "effective" mass of the sensor decreases which will inherently improve sensitivity. Second, low stiffness flexures effectively decouple the sensor and its vibrations from the base or substrate, thereby allowing the expression of high fidelity or high Q factor signals at the resonant frequency desired and designed for. Third, because the stiffness and mass of any attachments is minimized, the resonant sensing frequency will be higher, which directly correlates to higher sensitivity. In contrast, high stiffness attachments can highly or critically dampen the expression of the desired resonant frequency to the point that no sensing signal can be discerned. In a preferred embodiment, the sensor will be in a size domain where viscous damping in liquids is not inherent, thereby allowing the expression of high fidelity sensing signals in liquid media. Finally, the coextensive sensor which is effectively decoupled from its base or substrate will have a constant sensing response in mass/Hz along its length. This will allow the sensing surface to extend the length of the sensor without compromising the accuracy of the sensor.

The flexure 4 shown in FIG. 1 could be formed as a protrusion extending from one or both of the major exterior surfaces of the piezoelectric member. The protrusions could also be formed by attaching a flexible member (metal foil, plastic, e.g., polyimide, or the like) from one or more surfaces of the sensing element. Alternatively, flexure 4 could be formed as a protrusion from the passive planar member.

The floating bi-layer resonant sensor shown in FIGS. 1 and 2 also has fabrication advantages over the prior art. Because the active and passive planar members are coextensive and decoupled from the base or substrate, fabrication options are possible which will confer performance and cost benefits. Specifically, the active and passive planar members may be joined at the wafer level and then diced into individual sensors as shown in the figures. Dicing at the wafer level eliminates the variability inherent in assembling an individual active and passive die. The perfect alignment afforded by dicing will provide an exceptionally clean resonant frequency spectrum. Commercial wafer dicing saws are extremely accurate and repeatable so these coextensive sensors should also be exceptionally repeatable from sensor to sensor, thereby reducing or eliminating the need for screen testing of individual sensors. Because the active and passive planar members are coextensive and therefore used in a 1:1 ratio, less material will be required than in the prior art, with associated cost benefits.

Figure 3:
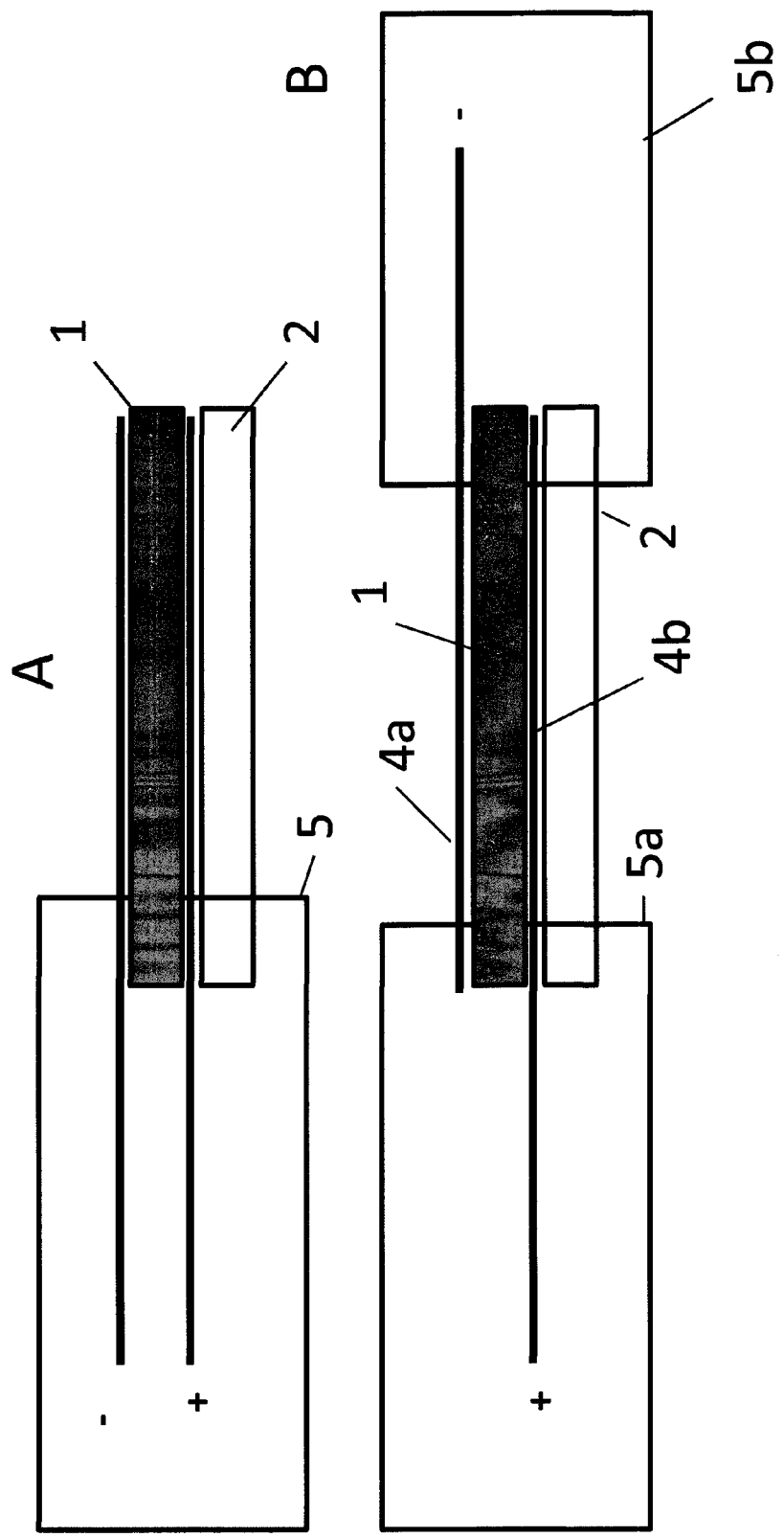
FIG. 3 is a side view of a resonant sensor of the present invention embodying "floating" bi-layer symmetry, in which the sensing element is embedded in a low bending modulus substrate(s) at one end (FIG. 3A) and at both ends (FIG. 3B).
Figure 4:
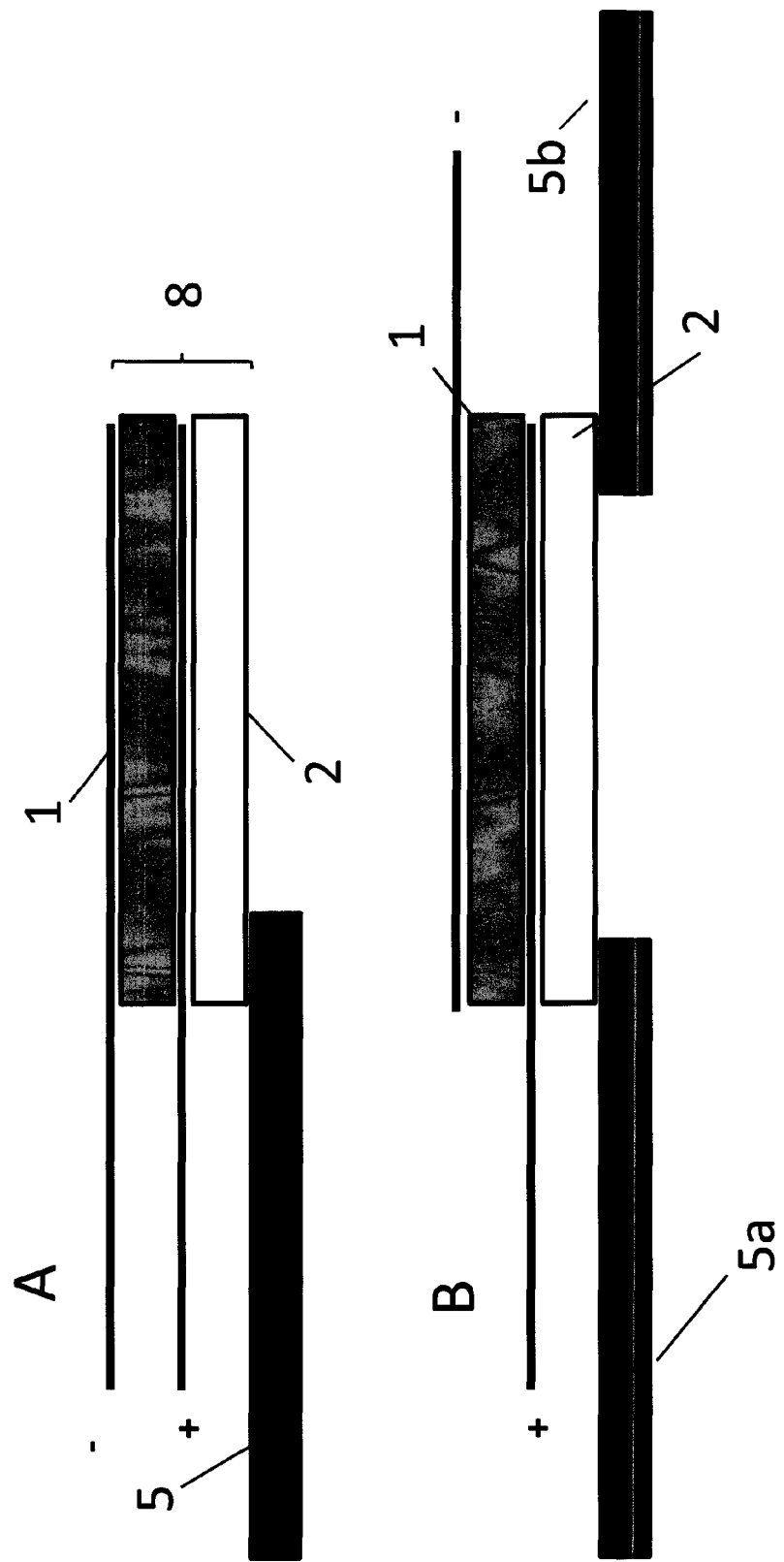
FIG. 4 is a side view of a resonant sensor of the present invention embodying "floating" bi-layer symmetry, in which the sensing element is mounted on a low bending modulus substrate(s) at one end (FIG. 4A) and at both ends (FIG. 4B).

FIGS. 3 and 4 show embodiments of the floating bi-layer sensor design in which one or both ends of the sensor are embedded in, or supported by a single base or substrate 5 or a pair of bases or substrates 5a and 5b. These designs allow the benefits of a coextensive assembly, while permitting the sensors to be anchored in or on one or more substrates which may be desirable in certain applications. If the stiffness of the substrate or anchor is sufficiently low in comparison to the stiffness of the coextensive sensing element, the fidelity of the sensing signal will still be adequate for sensitive analyte determinations. Accordingly, the sensing element may be supported by a flexible portion of at least one substrate to which at least one of the planar members of the sensing element is connected, such that the bending modulus of the flexible substrate portion is less than the bending modulus of the sensing element.

In the embodiment of the resonant sensor shown in FIG. 3, the mounting substrate 5 or any structure interposed between the mounting substrate and layered sensing element 8 is a flexible material selected such that the product of (the wavelength in the flexible material at the sensing frequency), (the surface area of the layered sensor element exposed to the flexible material), and (the density of the flexible material) must be an order of magnitude less than the mass of the layered structure AND the thickness of the flexible material in a direction normal to the layered sensor must be greater than the wavelength in the flexible material at the sensing frequency.

Figure 5:
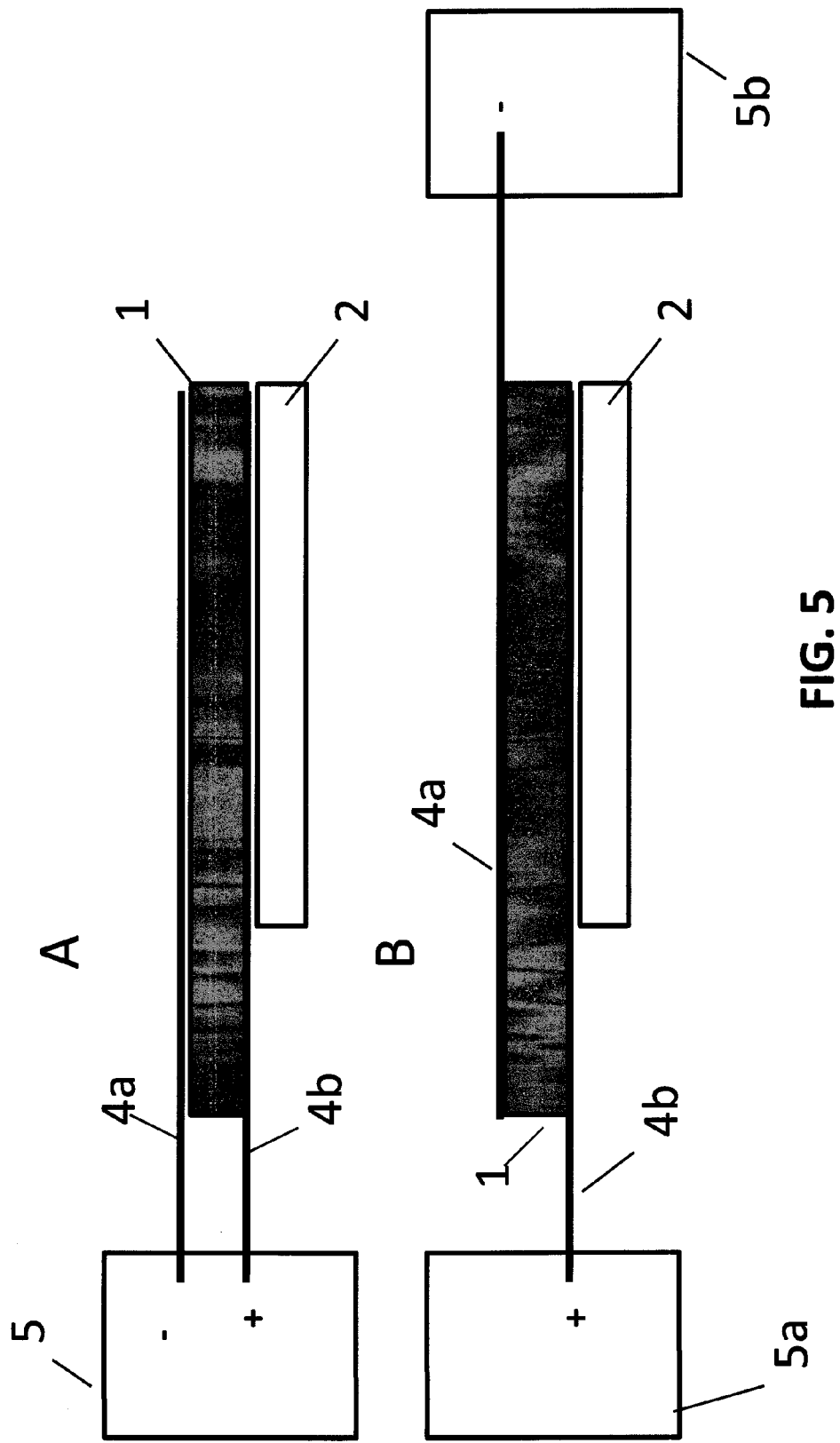
FIG. 5 is a side view of another resonant sensor design according to the present invention embodying "floating" bi-layer asymmetry, in which the active and passive planar members of the sensing element are not coextensive, and having alternative electrode configurations with electrodes disposed on opposite faces of the active planar member.
Figure 6:
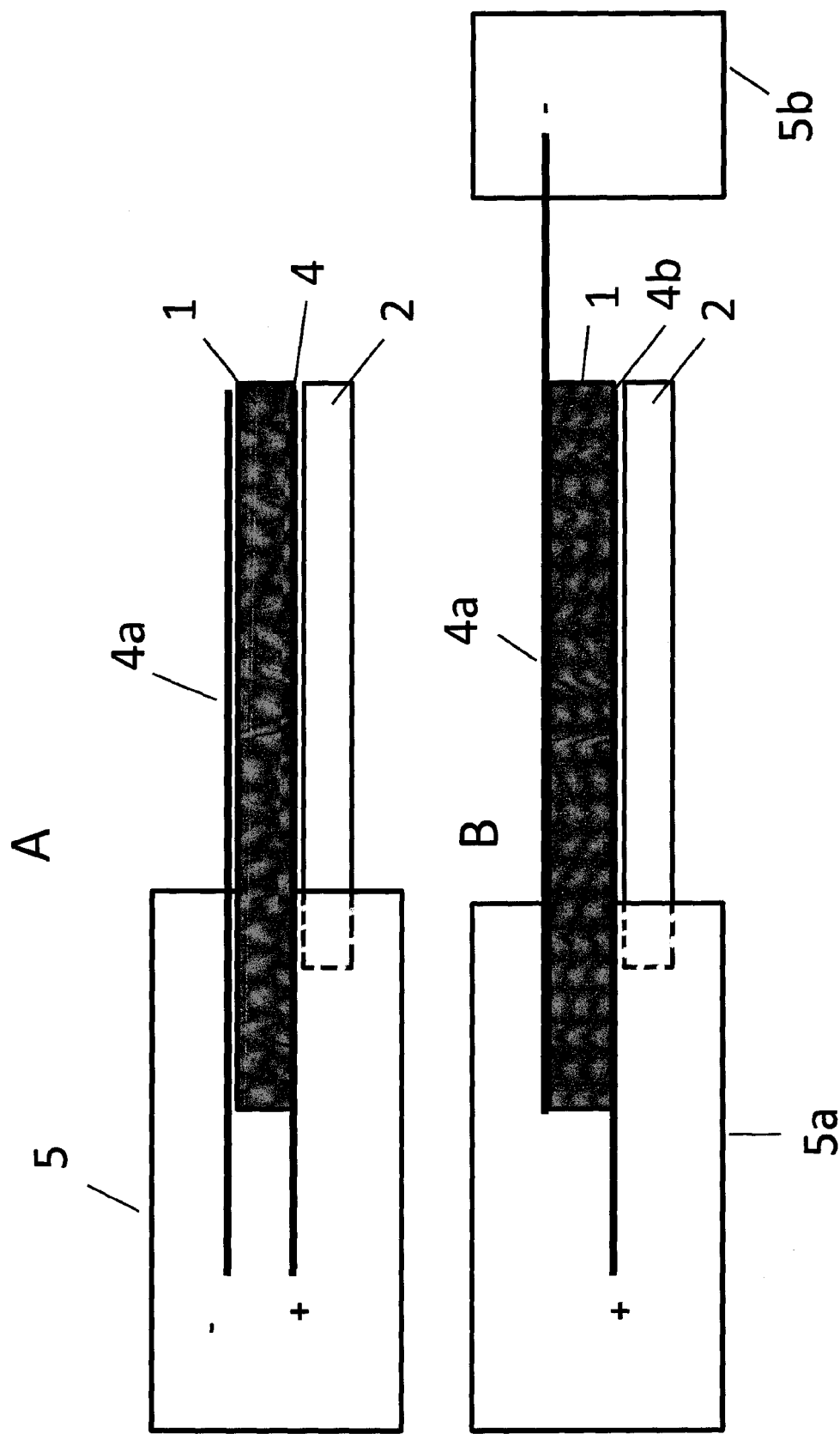
FIG. 6 is a side view of a resonant sensor of the present invention embodying "floating" bi-layer asymmetry, in which the active planar member and, optionally, the passive planar member (as indicated by the dotted line) is/are embedded in a low bending modulus substrate(s), with the same alternate electrode configurations shown in FIG. 2-5.

FIGS. 5 and 6 show sensors in which the active and passive planar members are asymmetric. The length dimensions of the active planar member of the sensing element may be greater than the length dimension of the passive planar member as shown in FIGS. 5 and 6 or vice versa. The degree of asymmetry will dictate how much the resonant sensing frequency is obscured by degenerate or unwanted modes which manifest themselves as unwanted noise in the sensing frequency spectrum. Nonetheless, this configuration can be very sensitive and steps can be taken to minimize the impact of degenerate modes. Specifically, the stiffness of the base material(s) or anchor(s) 5, 5a, 5b can be tailored to dampen the degenerate or unwanted modes, as in the devices shown in FIG. 4. Also, the electrode on one or both sides of the active member can be patterned in or on the portion not coextensive with the passive member to minimize the expression of degenerate modes, thereby preserving a useable sensing spectrum. In these embodiments, the flexural bending or extensional mode used for analyte determination may be selected from (i) the first vibration bending or extending mode along the width dimension of the sensing element, or (ii) an integer multiple of the first vibration bending mode along the width dimension.

In the embodiment of the resonant sensor shown in FIG. 6, the mounting substrate or any substrate interposed between the mounting substrate and layered sensor element is a flexible material selected such that the loss factor of the flexible material is sufficiently high that the section of the layered sensing element in contact with the flexible material exhibits critically damped resonance at the sensing frequency.

Figure 7:
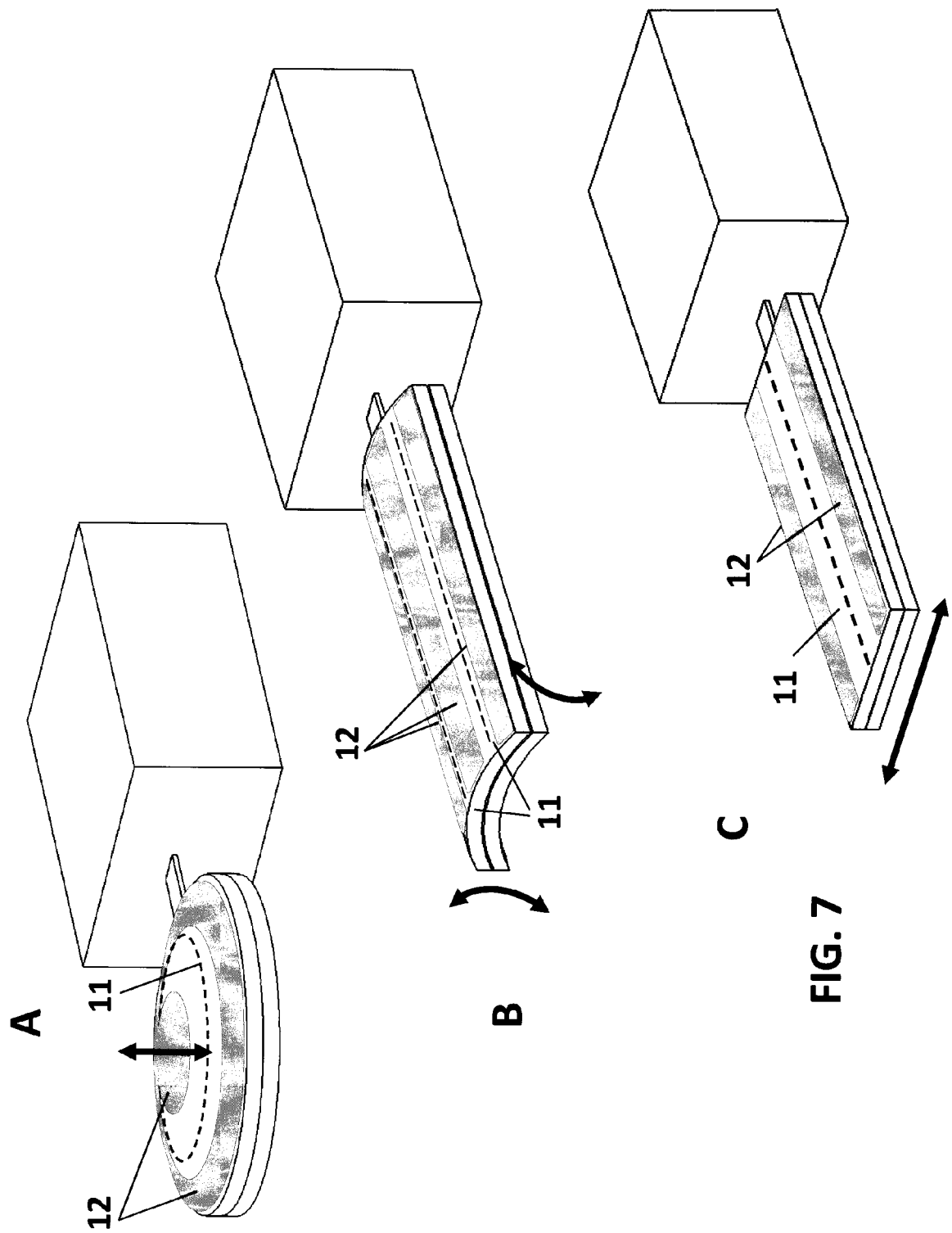
FIG. 7 includes perspective views of receptor placement in, and vibrational modes and associated nodal lines of resonant sensors according to the present invention embodying "floating" bi-layer symmetry.

FIGS. 7A and 7B show two possible geometries (circular and rectangular, respectively) for a floating bi-layer resonant sensor. These figures also show the vibrational modes (arrows) and associated nodal lines 11 of the sensors, as well as the capture agent sites 12. It is important to note where these nodal lines are because at these regions, the sensor will not give a response to analyte attachment. Exclusion of the capture agent (e.g. antibodies, ssDNA molecules) from the nodal regions will enhance the accuracy and repeatability for a given sensor to a target analyte binding.

The circular sensing element of the resonant sensor shown in FIG. 7A preferably has a thickness of from about 0.05 mm to about 5 mm and a radius of from about 0.25 mm to about 10 mm. In this embodiment, the total thickness of the planar members constituting the sensing element should be less than the radial dimension of the sensing element. The flexural bending or extensional mode used for analyte determination may be selected from (i) the first membrane bending mode along the radial dimension of the sensing element, or (ii) an integer multiple of the first membrane bending mode along the radial dimension.

The rectangular sensing element of the resonant sensor shown in FIG. 7B preferably has a thickness of from about 0.05 to about 5 mm and length and width dimensions of from about 0.25 mm to about 10 mm, and is most preferably approximately 0.250 mm thick, approximately 1.00 mm wide and approximately 4.0 mm long. In this embodiment, the total thickness of the planar members constituting the sensing element should be less than the in-plane length or width dimension of the sensing element. The flexural bending or extensional mode used for analyte determination may be selected from (i) the first vibration bending or extending mode along the length dimension of the sensing element or (ii) an integer multiple of the first vibration bending mode along the length dimension.

FIG. 7C shows the same rectangular sensor geometry as in FIG. 7B, but the nodal lines and sensing regions correspond to an extensional mode. The extensional nodal line is at the center of the rectangle and the optimal sensing locations are at the outer edges. In the case of an extensional mode the passive planer member is not required and it can be very thin, with a dimensional thickness ranging from about 0.010 um to about 250 um. The passive, deformable planar member in this case can be the thin electrode on the active deformable planar member. In FIG. 7C the extension mode can be orthogonal to the one shown, but still in the plane of the sensor planar members.

Figure 8:
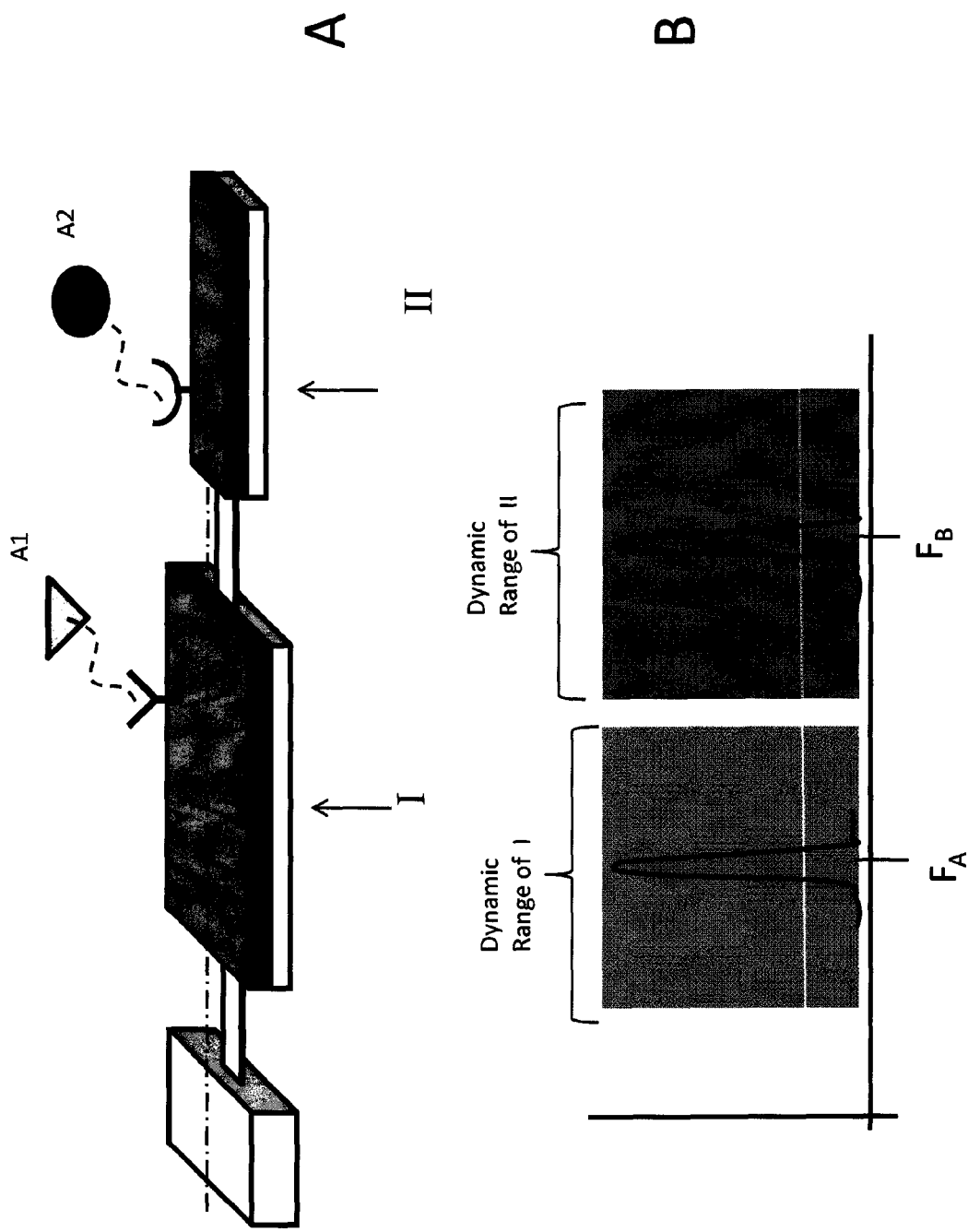
FIG. 8 includes an illustration of an assembly of concatenated resonance sensors in accordance with the present invention, which is capable of multiplex operation, whereby multiple analytes are detectable using the assembly of sensors, each sensing element having a capture agent for a different analyte (FIG. 8A) and a different dynamic range (FIG. 8B).

FIG. 8 shows two coextensive floating bi-layer resonant sensors, I and II, concatenated together. Each sensor element is designed to have a different baseline resonant frequency such that each sensor's dynamic range will be different and preferably will not overlap. Upon mass (analyte) attachment, the resonant frequency will shift lower until the analyte binding interaction reaches equilibrium with its solution, or the sensor surface receptor sites become saturated, or the end of its mechanical dynamic range is reached. Each sensor element will typically have a unique capture agent, with each sensor element binding a different analyte, A1, A2, etc. The expression "dynamic range", as used herein, refers to the portion of the frequency range in which a sensor's resonant frequency will operate due to analyte binding. The frequency width of the dynamic range can be determined by the amount of mass that can be loaded on the sensor before it becomes unresponsive. Practically speaking, the dynamic range will be determined by the maximum concentration of the analyte.

The sensor elements shown in FIG. 8 are connected in parallel such that both sensors can be interrogated with a single instrument to monitor their respective responses (e.g. impedance changes, phase angle changes, etc.). Sensors assemblies of this design enable multiplexing, which is very valuable from a time, cost and utility perspective. For example, in drug discovery, many candidate receptor pairs must be screened to find suitable drug candidates. The ability to parallel process or multiplex screening has apparent advantages. To create independent sensing elements, the elements must be effectively decoupled which is possible with the floating design of the present invention.

The method of fabricating the coextensive, floating bi-layer sensors shown in FIGS. 1 and 2 can be done by using largely off-the-shelf materials. The active material layer could be 125 um thick piezoelectric material (PZT) with metallization on either side. The passive layer could be 125 um thick alumina material with metallization on the bonded side. The two materials could be joined via a conventional or reactive soldering process. The bonded wafers could then be diced using a commercial diamond dicing saw or abrasive water micro-jet. The assembled sensor elements or die could then have electrodes soldered to the two electrodes of the PZT. The electrodes could be part of an injection molded assembly with a plastic substrate or base. The electrodes could be insulated with a polymer film such as polyimide. Since the bonded surface of the PZT would be inaccessible for electrode attachment, the alumina would have to have a conductive path or via for electrode attachment. The exposed side of the metalized PZT could be oxidized at some point to form a dense insulating layer. Titanium is readily oxidizable to form such a layer. A non-oxidizing metal could be deposited on the titanium prior to oxidizing as a small dot for subsequent electrode attachment. Alternatively, the oxide layer could be selectively etched back to expose conductive metal for attachment. There are many other ways (e.g. Parylene) to insulate the exposed electrode from conductive biological fluids. Provided the surface area of the exposed conductive parts of electrode are small relative to the total electrode surface area, such as the cross-sections exposed upon dicing, total or complete insulation of the electrodes may not be necessary. The exposed side of the alumina could have a thin layer of silicon oxide or some other material which can be readily coupled to capture agent molecules, thereby forming a ready sensing surface. The alumina layer itself could also be vapor deposited using a variety of techniques.

In FIGS. 3 and 4, the coextensive sensor assembly could be made in essentially the same way as described above. The assembly could be potted in a suitable epoxy or even fitted into a pre-molded slot containing electrodes which would make electrical contact upon insertion.

The assemblies shown in FIGS. 5 and 6 could be made using many of the same techniques as described above with a few exceptions. The alumina would need to be diced into bars or slotted in such a way that the stair-step between the PZT and alumina could be created. Alternatively, the two asymmetric pieces or die could be diced into their respective sizes and joined at the die level.

In each of the assemblies shown in FIGS. 3-6, the flexural stiffness about the axis of symmetry of the sensing element at the junction between the flexible coupling and the sensing element is preferably an order of magnitude less than the flexural stiffness of the sensing element, and the total mass of the flexible coupling intermediate its ends is preferably an order of magnitude less than the mass of the sensing element. In these embodiments, the activating force field is provided by an electric voltage source and the coupling element comprises an electrical conduction path from the voltage source to at least one side of the active planar member.

The concatenated assembly shown in FIG. 8 could also be assembled using similar techniques. The passive and active material planar members could be bonded in the form of wafers and subsequently diced. In this case, the electrodes would need to be daisy chained between the two assemblies. Alternatively, the passive and active material wafers could be diced down to die level and then assembled. Using die level assembly, the pieces could be bonded to a pre-cut electrode which would then form a concatenated sandwich, as shown in the drawing. In this case, only the remaining electrode would need to be daisy chained.

For analyte detection, an instrument would be needed to both excite and interrogate the sensor(s) using the same set of sensor electrodes. The instrument would need to be able to detect the resonant sensing signal and changes or shifts in this signal associated with analyte binding. When an analyte attaches to a capture agent on the sensor, the mass of sensor increases which causes the resonant frequency to shift lower. The frequency shift is indicative of detection and the amount or frequency of shift is directly proportional to the mass of the attached analyte, thereby allowing for quantification of the target analyte. As such, the instrument would need to be able to measure and track changes in resonant frequency. The detection frequencies would typically be in the 1-5 MHz range for which off-the-shelf circuitry is commercially available. However, there are a variety of ways to identify and track the sensor's resonant frequency changes such as the electrical properties of the active material (i.e.—impedance) or the real part of the impedance (i.e.—resistance) or the imaginary part of the impedance (i.e.—reactance) or the amplitude of the impedance or the phase angle of the impedance. The amplitude of vibration at resonance frequency could be measured externally using a laser or laser Doppler Velocimetry. Capacitive changes between the layered sensing structure and parallel electrodes of a base structure could also be correlated to resonant frequency changes and, therefore, could also be used in a measurement scheme. Typically, the instrument would also have a fluid interface for sensors, reagents and the biological sample fluid. The sensor could operate in a flow cell or micro-titer sample well. A flow cell is sometimes desirable to facilitate bringing scarce analytes in contact with the sensor surface when the analytes do not naturally diffuse well, such as cells or bacteria. However, the sensors would also work perfectly well in sample well volumes.

With such a sensor and detection system, a wide range of analytes could be detected. Representative examples of target analytes and binding partners that comprise specific binding pair members suitable for use in the present invention include, without limitation, antigen-antibody, DNA or RNA molecules-complementary sequences, receptor-hormone, receptor-ligand, agonist-antagonist, avidin-biotin and virus-receptor pairs. Still other specific binding pair members that may be determined in accordance with this invention will be apparent to those skilled in the art.

Members of specific binding pairs, e.g., protein or nucleic acid molecules, may be immobilized to a surface of the sensing element using techniques well known in the art. These include, for example, covalent binding (with or without spacer or linker groups), chemical cross-linking or physical adsorption. For example, one or more sites on the surface of the sensing element at which the capture agent is to be disposed may be derivatized with a chemical functional group appropriate for covalent binding to the capture agent. Chemistries useful for this purpose are described in the Campbell & Mutharasan (2005) articles cited above. See also, Rijal and Mutharasan, Anal. Chem., 79: 7392-7400 (2007). Alternative binding chemistries familiar to those skilled in the art may also be used. The capture agent may be immobilized in a one or two dimensional array.

The capture agent may also be an absorbent material, e.g., a polymeric material, which is effective to absorb an analyte of interest.

The sensing surface would be exposed to a solution containing the capture agent (e.g. antibodies, ssDNA molecules) which would bind to the sensing surface, then pre-treated with an appropriate surface chemistry that would readily bind the capture agent to the sensors. The resonant frequency of the sensor could be monitored during capture agent binding, also known as immobilization. The degree of resonant frequency shift would provide a real-time quality control to ensure the appropriate amount of receptor was bound to the sensor. Analyte detection would involve exposing the sensor with capture agent immobilized thereon to a sample containing suspected target analyte(s). Upon analyte binding to the sensor, the resonant frequency would shift downwards in proportion to the amount of binding. Several techniques could be used for calibrating the sensor response in a particular fluid. One technique is to expose the sensor to the sample fluid which is devoid of analyte to establish a baseline resonant frequency. A second technique would be to use two sensors in the sample fluid containing the analyte. One sensor would have capture agent immobilized thereon and the other would have no capture agent. The capture agent-free sensor would serve as a reference.

Subsequent to analyte binding and detection, a secondary antibody could be added to the sample which would bind to exposed sites on the analyte attached to the sensor. This technique could be used for two purposes. In the first case, secondary antibody could be used to "amplify" the detection signal because the secondary antibody would add additional mass to the sensor. The other purpose of a secondary antibody would be to discriminate between analytes bound to the sensor when the sensor is associated with capture agents for more than one analyte.

In one embodiment, the method of the present invention may be used for nucleic acid determinations. Specific analytes include cDNA molecules, cRNA molecules, DNA molecules, RNA molecules, RNAi molecules, pRNA molecules, and the like. When the target nucleic acid molecule hybridizes to its complementary single stranded capture agent immobilized on the sensing element, the resonant sensor may thereafter be exposed to polymerase activity to increase the mass of the analyte. This may be done after removal of the resonant sensor from the test medium. Alternatively, the sensor with analyte captured thereon may be exposed to polymerase activity directly in the test medium, e.g., serum.

The resonant sensors described above may be used for analyte determinations in liquid and gaseous test medium. When the sensors are operated in a liquid or gaseous environment, however, fluid damping tends to reduce the resonant response, and the magnitude of the reduction is related to the size of the device and the nature of fluid. In order to counter this damping effect, the layered sensing element of the resonant sensor that is to be used in a liquid environment is designed such that its mass per unit length along the bending direction is two orders of magnitude greater than the reciprocal square root of the resonance frequency used for sensing. Also, the layered sensing element of the resonant sensor that is to be used in a gaseous environment is designed such that its mass per unit length along the bending direction is greater than the reciprocal square root of the resonance frequency used for sensing.

The resonant sensor of this invention could also be used to monitor and measure kinetics between the capture agent immobilized thereon and the target analyte (i.e. the rates of complex formation ($k_a$) and dissociation ($k_d$)). When sensors with immobilized capture agent are exposed to a solution containing analytes, a sensor response (frequency shift) will take place over time until solution equilibrium is reached. Conversely, when the sensor with bound analyte is exposed to a solution with no analyte, the analytes will dissociate from the capture agent. Kinetics can also be determined by varying the excitation voltage of the sensor. Increasing the excitation voltage of the sensor will eventually cause bound analytes to dissociate. The sensor flexural displacements increase with increasing voltage which increases the displacement velocity and the inertial forces on bound analytes. Eventually, the increasing inertial forces will break the bonds between receptor and analyte. The energy required to break these bonds provides a proportional measure of binding energies.

The following examples describe the invention in further detail. These examples are provided for illustrative purposes only, and should in no way be considered as limiting the invention.

Example 1

Sensors were fabricated using 125 um PZT and 125 alumina. The materials were wafer bonded using epoxy or solder and subsequently diced to singulate individual sensor assemblies creating sensors with coextensive symmetry and asymmetry. The dimensions evaluated ranged from 0.75 to 1.25 mm wide and up to 6 mm long. Electrode wires were soldered and fixed with conductive epoxy. Sensors were fabricated "floating" and anchored in epoxy. The resonant frequency, associated spectrum and signal quality (Q) were examined using an impedance analyzer. The sensor variations built verified behavior expected from finite element modeling.

Example 2

Figure 9:
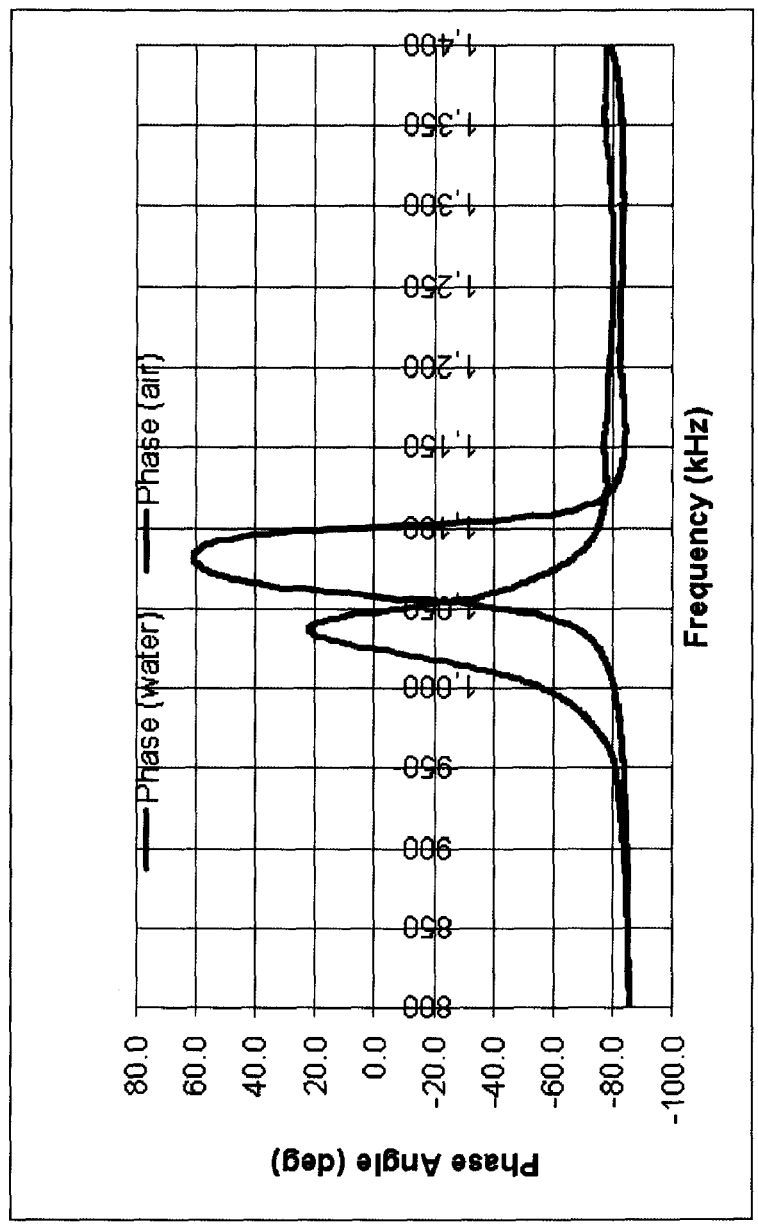
FIG. 9 is a graphical representation of a resonant frequency spectrum produced by a resonant sensor embodying the present invention, in which phase angle is shown as a function of frequency (kHz).

Devices were fabricated ranging from 1.5×1 mm to 2.0×1 mm in which the active and passive planar members were coextensive, having equal length and width. Two different methods were successfully used to fabricate these devices. In one method, a 1.5×1 mm PZT layer having a thickness of 125 µm, which served as the active member, was joined to a passive, alumina layer having the same dimensions. The alumina layer was metalized and soldered to the PZT layer. The alumina layer had a solder filled via which allowed for electrodes to be attached to either side of the assembly. The electrodes were metal strips and were attached with conductive epoxy. The structure of the resulting device corresponds generally to that illustrated in FIG. 1. This device produced the spectrum shown in FIG. 9. An alternate assembly method was also successfully used, substituting glass for alumina as the passive member, which was attached to the PZT layer by means of epoxy. A metal strip electrode was attached to the exposed surface of the PZT. A metal wire electrode was affixed to the opposite surface of the PZT layer, which was bonded to the glass layer and contacted at one of the diced edge surfaces, using a fine wire and conductive epoxy. The resulting structure corresponds generally to that shown in FIG. 1. The device produced a spectrum similar to that shown in FIG. 9.

A number of patent documents and non-patent documents are cited in the foregoing specification in order to describe the state of the art to which this invention pertains. The entire disclosure of each of the cited documents is incorporated by reference herein.

While various embodiments of the present invention have been described and/or exemplified above, numerous other embodiments will be apparent to those skilled in the art upon review of the foregoing disclosure. The present invention is, therefore, not limited to the particular embodiments described and/or exemplified, but is capable of considerable variation and modification without departure from the scope of the appended claims. Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All resonant sensors and methods of use thereof that embody the present invention can, in alternate embodiments, be more specifically defined by any of the transitional terms "comprising", "consisting essentially of" and "consisting of".

What is claimed is:

1. A resonant sensor for determining the presence, amount or binding kinetics of an analyte in a test medium, said sensor being operable under the influence of an activating force field and comprising:
    an active, deformable planar member;
    a passive, deformable planar member attached to said active, deformable planar member, forming a pliable, layered sensing element having flexural stiffness and a resonant flexural bending or extensional mode for analyte determination and at least one axis of symmetry;
    at least one substrate coupled to said layered sensing element by at least one flexible coupling element having a first end joined to said substrate and a second end joined to said sensing element, said substrate having a flexible portion and permitting said vibration of said sensing element;
    said layered sensing element being supported by said flexible portion of said substrate to which at least one of the planar members of said sensing element is connected, the flexible substrate portion having a bending modulus which is less than the sensing element bending modulus; and
    a capture agent for said analyte associated with at least one exterior surface site of said sensing element, said capture agent being one member of a specific binding pair and the other member of said specific binding pair being said analyte;
    said sensing element with associated capture agent being caused to vibrate at a determinable resonance frequency by said activating force field operating on said active, deformable planar member, said activating force field inducing in said sensing element a uniform bending moment or extensional force component that is substantially parallel or perpendicular to said at least one axis of symmetry.

2. The resonant sensor according to claim 1, wherein said passive, deformable planar member is coextensive with said active, deformable planar member.

3. The resonant sensor according to claim 1, wherein said active, deformable planar member comprises a piezoelectric material, and said activating force field is an electric field.

4. The resonant sensor according to claim 1, wherein said active, deformable planar member comprises an electrostrictive material, and said activating force field is an electric field.

5. The resonant sensor according to claim 1, wherein said active, deformable planar member comprises a magnetostrictive material, and said activating force field is a magnetic field.

6. The resonant sensor according to claim 1 having flexural stiffness about the axis of symmetry of said sensing element at the junction between the flexible coupling element and the sensing element, which is an order of magnitude less than the flexural stiffness of the sensing element, and the total mass of the flexible coupling element intermediate its ends is an order of magnitude less than the mass of the sensing element.

7. The resonant sensor according to claim 6, wherein said activating force field is provided by an electric voltage source and said coupling element comprises an electrical conduction path from said voltage source to at least one side of said active planar member.

8. The resonant sensor according to claim 1, wherein both the active and passive planar members of said sensing element are embedded in the flexible portion of said at least one substrate.

9. The resonant sensor according to claim 1, wherein the in-plane shape of the sensing element is selected from the group consisting of a circular, square or rectangular shape.

10. The resonant sensor according to claim 9, wherein the in-plane shape of the sensing element is rectangular and the length dimension of said active planar member is greater than the length dimension of said passive planar member.

11. The resonant sensor according to claim 9, wherein the in-plane shape of the sensing element is rectangular and the length dimension of said passive planar member is greater than the length dimension of the active planar member.

12. The resonant sensor according to claim 10 or 11, wherein the flexural bending or extensional mode used for analyte determination is selected from (i) the first vibration bending or extending mode along the width dimension of the sensing element, or (ii) an integer multiple of said first vibration bending mode along said width dimension.

13. The resonant sensor according to claim 9, wherein the in-plane shape of the sensing element is circular and the total thickness of the planar members constituting said sensing element is less than the radial dimension of said sensing element.

14. The resonant sensor according to claim 13, wherein the flexural bending or extensional mode used for analyte determination is selected from (i) the first membrane bending mode along the radial dimension of said sensing element, or (ii) an integer multiple of said first membrane bending mode along said radial dimension.

15. The resonant sensor according to claim 13, wherein the thickness of said layered sensing element is from about 0.05 mm to about 5 mm and the radial dimension is from about 0.25 mm to about 10 mm.

16. The resonant sensor according to claim 9, wherein the in-plane shape of the sensing element is rectangular or square and the total thickness of the planar members constituting said sensing element is less than the in-plane length or width dimension of said sensing element.

17. The resonant sensor according to claim 16, wherein the flexural bending or extensional mode used for analyte determination is selected from (i) the first vibration bending or extending mode along the length dimension of said sensing element or (ii) an integer multiple of said first vibration bending mode along said length dimension.

18. The resonant sensor according to claim 16, wherein the thickness of said layered sensing element is from about 0.05 mm to about 5 mm and the length and width dimensions are from about 0.25 mm to about 10 mm.

19. The resonant sensor according to claim 18, wherein the dimensions of the layered sensing element are 0.250 mm thick, 1.0 mm wide and 4.0 mm long.

20. The resonant sensor according to claim 18, wherein the thickness of the passive, deformable planar member is about 0.010 um to about 250 um.

21. The resonant sensor according to claim 18, wherein the passive, deformable planar member is in the form of a thin electrode on the active, deformable planar member.

22. The resonant sensor according to claim 1, wherein said in-plane shape of the sensing element is rectangular and said capture agent is disposed on the exterior surface of said element at sites spaced apart from nodal points or lines that are characteristic of said flexural bending or extensional mode.

23. The resonant sensor according to claim 1, wherein said activating force activates the active, deformable planar member, causing portions of the sensing element adjacent to nodal points or lines to flex out of the plane or extend in plane of the sensing element, said nodal points or lines being characteristic of said flexural bending or extensional mode.

24. An apparatus for determining the presence, or amount or binding kinetics of an analyte in a test medium, said apparatus, comprising a resonant sensor as claimed in claim 1, and a device operable to determine said resonance frequency.

25. A system for determining the presence, or amount or binding kinetics of an analyte in a test medium, said system, comprising an assembly of concatenated resonance sensors, as claimed in claim 1, and a device operable to determine the resonance frequency of the resonant sensors in said assembly.

26. The system according to claim 25, wherein each of the concatenated sensors has a different dynamic range.

27. The system according to claim 25, wherein each of the resonant sensors in said assembly is operable under the influence of a common activating force field, and the resonance frequency at which the sensing element of each said resonance sensor vibrates is determined by a common frequency determining device.

28. The system according to claim 25, wherein each of the resonant sensors in said assembly has disposed on the surface thereof a capture agent which is different from the capture agent on any other sensing element in said assembly, whereby each resonant sensor captures a different analyte.

29. The resonant sensor according to claim 1, wherein said specific binding pair member and the analyte captured by said specific binding pair member form a binding pair selected from the group consisting of nucleic acid (RNA or DNA) fragments-complementary sequences, antigen-antibody, receptor-hormone, receptor-ligand, agonist-antagonist, avidin-biotin, virus-receptor.

30. The resonant sensor according to claim 29, wherein said binding pair comprises nucleic acid fragment-complementary sequence.

31. The resonant sensor according to claim 30, wherein one binding pair member is selected from the group of DNA molecules, RNA molecules, cDNA molecules, cRNA molecules, RNAi molecules and pRNA molecules.

32. The resonant sensor according to claim 1, wherein the at least one flexible coupling element is critically damped at the resonance frequencies used for analyte determination.

33. The resonant sensor according to claim 1 wherein the flexural stiffness about the axis of symmetry of said sensing element at the junction between said flexible portion(s) and the sensing element is an order of magnitude less than the flexural stiffness of the sensing element, and the total mass of said flexible portion(s) is an order of magnitude less than the mass of the sensing element.

34. A method for determining an analyte of interest in a test medium suspected to contain said analyte, which is a member of a specific binding pair, said method comprising:
 a. providing at least one resonant sensor as claimed in claim 1;
 b. establishing a reference resonance frequency;
 c. contacting said sensor with a medium suspected to contain an analyte of interest, for a time sufficient for said specific binding pair member to bind analyte of interest present in said medium;
 d. determining a test resonance frequency of said sensor after contact with said medium, a shift between the test resonance frequency and the reference resonance frequency providing a qualitative indication of target analyte in said test medium.

35. The method of claim 34 further comprising quantitatively determining the analyte of interest in said test medium by measuring said frequency shift associated with analyte binding, the difference in frequency being related to the amount/mass of the bound analyte.

36. The method of claim 34 or 35, wherein said capture agent comprises a single stranded nucleic acid molecule comprised of a series of nucleotide(s) and the test medium contacted with said resonant sensor is suspected of containing a target nucleic acid analyte comprising a nucleotide sequence complementary to said single stranded nucleic acid.

37. The method of claim 36, further comprising exposing said resonant sensor to polymerase activity.

38. The method of claim 34, wherein said nucleic acid molecule is selected from the group of DNA molecules, RNA molecules, cDNA molecules, cRNA molecules, RNAi molecules and pRNA molecules.

39. A resonant sensor for determining the presence, amount or binding kinetics of an analyte in a test medium, said sensor being operable under the influence of an activating force field and comprising:
- an active, deformable planar member, comprising a piezoelectric material and having first and second metallized surfaces;
- a passive, deformable planar member, attached to a metalized surface of said active deformable planar member, forming a pliable, layered sensing element having flexural stiffness and a resonant flexural bending or extensional mode for analyte determination and at least one axis of symmetry;
- at least one substrate coupled to said layered sensing element by at least one flexible coupling element having a first end joined to said substrate and a second end joined to said sensing element, said substrate supporting and permitting said vibration of said sensing element; and
- a capture agent for said analyte associated with at least one exterior surface site of said sensing element;
- said sensing element with associated capture agent being caused to vibrate at a determinable resonance frequency by said activating force field operating on said active, deformable planar member, said activating force field inducing in said sensing element a uniform bending moment or extensional force component that is substantially parallel or perpendicular to said at least one axis of symmetry, said activating force field being an electric field.

40. The resonant sensor according to claim 39, wherein said capture agent for said analyte is an absorbent material effective to absorb said analyte.

41. The resonant sensor according to claim 40, wherein said absorbent material is a polymeric absorbent.

* * * * *